US012269028B2

United States Patent
Pennie

(10) Patent No.: US 12,269,028 B2
(45) Date of Patent: Apr. 8, 2025

(54) VENTED DUAL PORT CENTRIFUGE TUBE

(71) Applicant: Patrick Pennie, Fort Myers, FL (US)

(72) Inventor: Patrick Pennie, Fort Myers, FL (US)

(*) Notice: Subject to any disclaimer, the term of this patent is extended or adjusted under 35 U.S.C. 154(b) by 230 days.

(21) Appl. No.: 17/580,894

(22) Filed: Jan. 21, 2022

(65) Prior Publication Data

US 2022/0226811 A1 Jul. 21, 2022

Related U.S. Application Data

(60) Provisional application No. 63/139,934, filed on Jan. 21, 2021.

(51) Int. Cl.
*B01L 3/00* (2006.01)

(52) U.S. Cl.
CPC ..... *B01L 3/5021* (2013.01); *B01L 2200/0684* (2013.01); *B01L 2200/0689* (2013.01); *B01L 2300/0681* (2013.01); *B01L 2300/0832* (2013.01); *B01L 2400/0409* (2013.01); *B01L 2400/0478* (2013.01)

(58) Field of Classification Search
CPC .......... B01L 3/5021; B01L 2200/0684; B01L 2200/0689; B01L 2300/0681; B01L 2300/0832; B01L 2400/0409; B01L 2400/0478
See application file for complete search history.

(56) References Cited

U.S. PATENT DOCUMENTS

| | | | |
|---|---|---|---|
| 4,057,050 A | 11/1977 | Sarstedt | |
| 4,142,668 A | 3/1979 | Lee | |
| 4,152,270 A | 5/1979 | Cornell | |
| 4,154,690 A | 5/1979 | Ballies | |
| 4,443,345 A | 4/1984 | Wells | |
| 6,123,655 A | 9/2000 | Fell | |
| 6,733,433 B1 | 5/2004 | Fell | |
| 6,835,353 B2 | 12/2004 | Smith | |
| 7,179,391 B2 | 2/2007 | Leach | |
| 7,445,125 B2 | 11/2008 | Ellsworth | |
| 7,806,276 B2 | 10/2010 | Leach | |

(Continued)

FOREIGN PATENT DOCUMENTS

GB 2393670 A 4/2004
WO WO 2005039773 5/2005

OTHER PUBLICATIONS

U.S. Appl. No. 10/987,672, filed Apr. 27, 2021, Pennie.

*Primary Examiner* — Jill A Warden
*Assistant Examiner* — Alex Ramirez
(74) *Attorney, Agent, or Firm* — William E. Noonan

(57) ABSTRACT

A vented dual port centrifuge tube includes a tubular receptacle having upper and lower ends. A first common inlet and outlet port is formed in the upper end and a second common inlet and outlet port is formed in the lower end. A piston is sealably and slidably mounted within a chamber of the receptacle. A vent is supported in the upper end of the receptacle and a flexible vent pipe attached to the piston is communicably interconnected between the vent and a lower region of the chamber between the piston and the lower end of the receptacle. Air pressure in the lower region of the receptacle is equalized or neutralized as biological fluids and separated constituent components are introduced into and aspirated from the receptacle through the common inlet ports.

15 Claims, 12 Drawing Sheets

(56) References Cited

U.S. PATENT DOCUMENTS

| | | | |
|---|---|---|---|
| 7,976,796 B1 | 7/2011 | Smith | |
| 9,421,319 B2 | 8/2016 | Hwang | |
| 9,440,243 B2 | 9/2016 | Chapman | |
| 9,573,130 B2 | 2/2017 | Hassouneh | |
| 9,610,590 B2 | 4/2017 | Hamandi | |
| 10,183,042 B2 | 1/2019 | Leach | |
| 10,300,481 B2* | 5/2019 | Pennie | G01N 33/491 |
| 10,537,888 B2 | 1/2020 | Pennie | |
| 10,576,130 B2 | 3/2020 | Matuska | |
| 10,773,262 B2 | 9/2020 | Camisani | |
| 2003/0060352 A1* | 3/2003 | Dolecek | B04B 5/0428 494/18 |
| 2004/0251217 A1 | 12/2004 | Leach | |
| 2004/0256331 A1 | 12/2004 | Arking | |
| 2005/0065454 A1 | 3/2005 | Manoussakis | |
| 2005/0109716 A1 | 5/2005 | Leach | |
| 2005/0124073 A1 | 6/2005 | Freund | |
| 2005/0274679 A1 | 12/2005 | Kao | |
| 2006/0196885 A1 | 9/2006 | Leach | |
| 2006/0273050 A1 | 12/2006 | Higgins | |
| 2006/0278588 A1 | 12/2006 | Woodell-May | |
| 2009/0221075 A1 | 9/2009 | Dorian | |
| 2010/0140182 A1 | 6/2010 | Chapman | |
| 2011/0284460 A1 | 11/2011 | Leach | |
| 2014/0205514 A1 | 7/2014 | Hwang | |
| 2015/0367064 A1 | 12/2015 | Pennie | |
| 2016/0030661 A1 | 2/2016 | Hwang | |
| 2017/0028137 A1 | 2/2017 | Mirabito | |
| 2017/0266664 A1 | 9/2017 | Lukhaub | |
| 2018/0353954 A1* | 12/2018 | Pennie | B04B 5/0442 |

\* cited by examiner

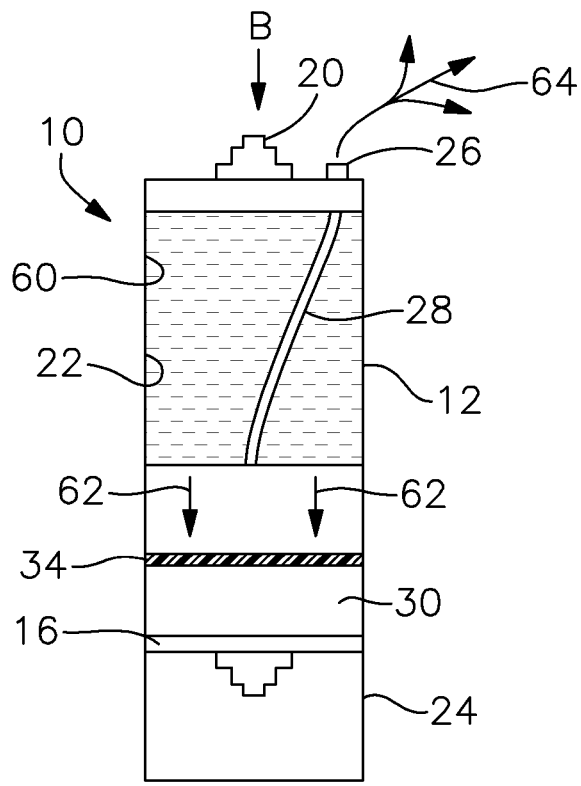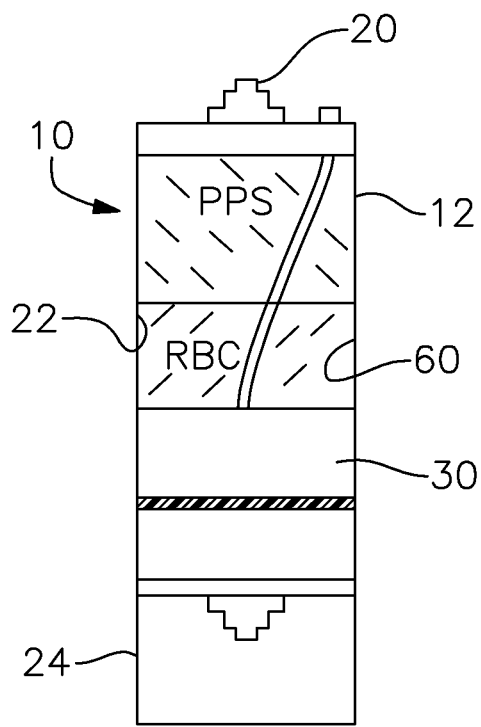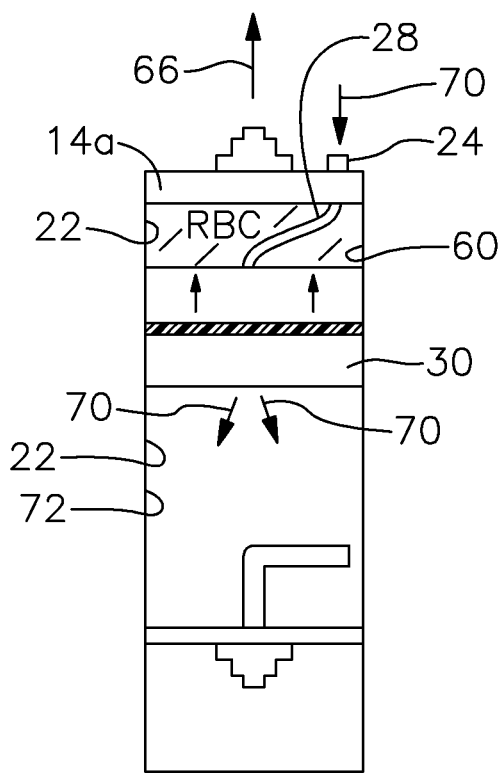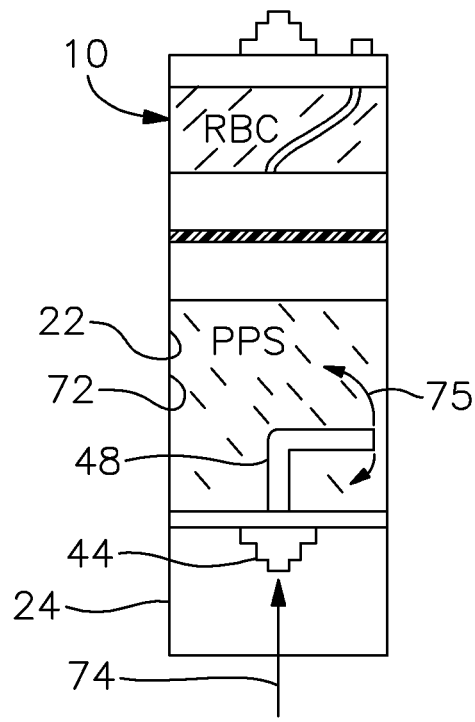

VENTED DUAL PORT CENTRIFUGE TUBE

RELATED APPLICATION

This application claims the benefit of Provisional Application Ser. No. 63/139,934 filed Jan. 21, 2021.

FIELD OF THE INVENTION

This invention relates to a vented dual port centrifuge tube used to effectively separate and concentrate fluid biological products such as blood, stem cells, bone marrow aspirate and the like into constituent components, which may be conveniently and efficiently aspirated following centrifugation. The apparatus is particularly effective for sequestering platelet rich plasma and bone marrow aspirate for use in surgical, medical and veterinary procedures.

BACKGROUND OF THE INVENTION

Platelet-rich blood plasma is required for use in various medical procedures. This blood product is particularly effective due to its growth promoting features, which assist greatly in wound healing and bone regeneration. Presently, blood plasma with a high concentration of platelets is utilized for dental implants and other periodontal procedures, facial reconstruction, oral or maxillofacial surgery and chronic wound care. In order to obtain a required concentration of platelets, a blood sample normally must be centrifuged in order to separate the blood into its component blood products (i.e., plasma, red blood cells and platelets). The platelets, typically in a form of a white "buffy coat", are then separated from the blood sample and sequestered in concentrated form through aspiration. Conventional aspiration techniques often fail to provide a satisfactory concentration of platelets. Cross-contamination between the constituent products is frequently encountered. In recent years there has been an increasing demand for improved, cost effective and easy to operate centrifuge tubes that facilitate the sequestration of platelets and provide for highly pure platelet production, while minimizing cross-contamination between blood components.

I have developed various centrifuge assemblies as disclosed in U.S. Pat. Nos. 6,835,353, 7,976,796, 10,300,481 and 10,537,888 to address the foregoing needs and concerns. These products have achieved superior results and proven to constitute a significant improvement over the prior art. I have also developed a dual piston centrifuge tube as disclosed in U.S. Pat. No. 10,987,672. This product especially reduces the risk of cross contamination of sequestered PRP by air and other blood components present in the tube. My dual piston device employs a simple and failure-resistant construction that enables PRP and other constituents of fluid biological products to be obtained in a quick, convenient and reliable manner for use in various surgical, medical and veterinary applications.

Notwithstanding the improved results achieved by the foregoing products, an ongoing need continues to exist for improved centrifuge tubes of this type. In particular, it is desirable to employ a construction that is constructed as simply as possible in order to reduce manufacturing complexity and the potential for product failure. In addition, the user should be able to operate the tube more conveniently and smoothly, and without encountering undue sticking or resistance caused by pressure imbalances produced in the tube during the sequestration process. This will better enable users to obtain high quality PRP, bone marrow aspirate and other desired biological constituents.

SUMMARY OF THE INVENTION

It is therefore an object of the present invention to provide a simple, efficient and highly reliable centrifuge tube that allows blood, bone marrow aspirate and other fluid biological products to be effectively sequestered and concentrated into constituent components and conveniently aspirated following separation.

It is a further object of this invention to provide a dual port centrifuge tube featuring a simpler and less costly construction, and which is easier to use and less prone to product failure than existing centrifuge tubes.

It is a further object of this invention to provide a dual port centrifuge tube that is effectively, resists cross-contamination and yields a high quality biological fluid aspirate.

It is a further object of this invention to provide a vented dual port centrifuge tube employing a single piston and unique, highly efficient vent pipe construction that effectively equalizes air pressure imbalances in the tube and enables the piston to exhibit a smoother resistance-free movement, which facilitates and improves usage of the tube.

It is a further object of this invention to provide a dual port centrifuge tube which enables the manufacture of improved, highly concentrated and pure PRP in a relatively uncomplicated, quick, efficient, safe and effective manner.

It is a further object of this invention to provide a dual port centrifuge tube that enables blood product and other fluid biological products to be aspirated in a reliable and extremely safe manner.

It is a further object of this invention to provide a vented dual port centrifuge tube that permits a host of chemicals, bodily fluids, and other fluid biological products to be separated and individually aspirated with a low risk of cross contamination or airborne contamination.

It is a further object of this invention to provide a dual port centrifuge tube that is particularly effective for sequestering a high concentration of platelet-rich plasma for use in various medical, surgical and veterinary procedures.

It is a further object of this invention to provide a dual port centrifuge tube that may be used effectively and efficiently for separating and aspirating a wide range of biological products, including but limited to blood, stem cells, bone marrow aspirate, etc.

It is a further object of this invention to provide a uniquely vented centrifuge tube that eliminates the unbalanced operation commonly exhibited by known centrifuge tubes during centrifugation by reducing the amount of air trapped in the tube.

It is a further object of this invention to provide a dual port centrifuge tube featuring a configuration and construction that enables PRP and other biological fluids to be more effectively and completely recovered from the tube following centrifugation.

This invention results from a realization that a centrifuge tube for separating and aspirating constituent components of a fluid biological product may be significantly and efficiently simplified and yet provide extremely effective results by employing two opposing common inlet and outlet ports at respective ends of the tube, a single piston or diaphragm that is slidable through the tube and a unique flexible vent pipe interconnected between a capped upper end of the tube and the piston. When such a centrifuge tube is operated in accordance with this invention, it effectively equalizes or neutralizes pressure within the tube during injection and aspiration steps and therefore allows the user to perform such steps smoothly, easily and with less resistance or sticking exhibited by the piston. At the same time, the tube is constructed to produce a concentrated and high quality aspirate that may be employed in various surgical, medical and veterinary applications.

This invention features a dual port centrifuge tube assembly that includes an elongate tubular receptacle having an interior chamber and closed upper and lower portions. A liquid impermeable piston is mounted within the chamber and is slidable through the chamber while maintaining sealing engagement with an interior surface of the receptacle. A first common inlet and outlet port is formed in the upper portion of the receptacle for communicating with an upper region of the interior chamber above the piston. A second common inlet and outlet port is formed through the lower portion of the tubular receptacle for communicating with a lower region of the interior chamber below the piston. A vent is formed through the upper portion of the receptacle and a flexible vent pipe is communicably interconnected between the vent and the piston in communication with the lower region of the chamber.

In a preferred embodiment, the upper portion of the tubular receptacle includes an upper cap through which the vent and the first common inlet and outlet port extend. The vent is preferably spaced apart and distinct from the first common inlet and outlet port. The lower portion of the tubular receptacle may include a substantially flat base through which the second common inlet and outlet port is formed to communicate with the lower region of the chamber. The first common inlet and outlet port communicates with the upper region of the chamber above the piston.

The piston may include a body that is sealably and slidably interengaged with the interior sidewall of the tubular receptacle. A passageway may extend vertically through the piston body. The passageway, which is preferably formed centrally through the piston body, may be communicably interconnected between the vent pipe and the lower region of the receptacle chamber. The piston body may further include upper and lower circumferential flanges that are attached to and extend upwardly and downwardly respectively from the piston body. The lower circumferential flange will have a diametric channel formed therein.

The second common inlet and outlet port may include a tubular stem that extends into the lower region of the chamber. The stem may include an elbow having a distal end disposed proximate the circumferential flange of the piston and proximate an interior surface of a sidewall of the receptacle.

A base may be attached to and depend from the lower portion of the tubular receptacle. Preferably, the base has a cylindrical shape that conforms to the shape and diameter of the tubular receptacle. The base supports the tubular receptacle above an underlying surface and the second common inlet and outlet port may be surrounded by and centrally disposed within the base.

In the preferred version of the tube, blood or other biological fluid is introduced into the upper chamber region of the tubular receptacle through the first common inlet and outlet port. This drives the piston downwardly through the receptacle such that air in the lower region of the chamber beneath the piston is pushed upwardly through the passageway of the piston body and through the vent tube. Such air is expelled through the vent in the top of the tube, which equalizes pressure in the tube. When the piston is fully lowered, the diametric channel receives the tubular stem of the second port. The tubular receptacle is then centrifuged a first time to separate the biological fluid into a pair of layers representing respective constituent components (e.g., red blood cells—RBC, and plasma platelet suspension—PPS). The user then aspirates the top sequestered fluid layer (e.g., PPS) through the first common inlet and outlet port. That aspirated constituent is then introduced through the second common inlet and outlet port in the lower end of the receptacle to occupy a lower region of the receptacle chamber. Again, air within the lower region is displaced through the vent tube and vent to equalize pressure within the tube. The receptacle is then centrifuged a second time to separate the fluid constituents into the respective layers within the lower chamber region. In cases where PPS has been introduced into the lower chamber region, the second centrifugation may produce an upper layer of platelet poor plasma (PPP) and a lower buffy coat layer comprising PPS and platelet rich plasma PRP. Most of the upper layer produced within the lower chamber region is then aspirated to leave a remaining fluid within the lower region. The tube is then agitated to mix the remaining fluid (e.g., to mix any remaining PPP with buffy coat). This mixed product is then aspirated, which, in the case of blood sequestration, yields a high quality PRP product.

In an alternative embodiment, the second common inlet and outlet port may be offset from the center of the closed lower portion of the tubular receptacle. In such embodiments, a semi-cylindrical base is attached to and depends from the lower end portion of the tubular receptacle such that the second common inlet and outlet port is positioned radially to be at least partially outside of the semi-cylindrical base. This provides syringe access to the second common inlet and outlet port when the centrifuge tube is used as described below.

In the alternative embodiment of the invention, the second common inlet and outlet port may include a tubular channel that extends into the interior chamber of the receptacle below the piston. The channel may have a diagonal or slanted upper end to facilitate aspiration of PRP or other constituent fluids from the receptacle. The semi-cylindrical base may include a longitudinal slot formed in the base to facilitate user access to the second common inlet and outlet port.

BRIEF DESCRIPTION OF THE DRAWINGS

Other objects, features and advantages will occur from the following description of a preferred embodiment and the accompanying drawings, in which:

FIG. 3 is a simplified elevational rear view of the preferred tube with a biological fluid, such as a blood sample, being introduced into the receptacle chamber above the piston;

FIG. 4 is a view similar to FIG. 3, which shows the tube after it is centrifuged a first time to separate the biological fluid into first and second constituent components, e.g., red blood cells and platelet plasma suspension (PPS);

FIG. 5 is a similar elevational view of the preferred tube wherein one of the separated constituents, e.g., PPS, is aspirated from the receptacle through the first common inlet and outlet port to raise the piston within the tubular receptacle;

FIG. 6 is a similar elevational view of the preferred tube that depicts the introduction of the previously aspirated component through the second common inlet and outlet port into a lower region of the receptacle chamber below the piston;

DETAILED DESCRIPTION OF PREFERRED EMBODIMENTS

Figure 1:
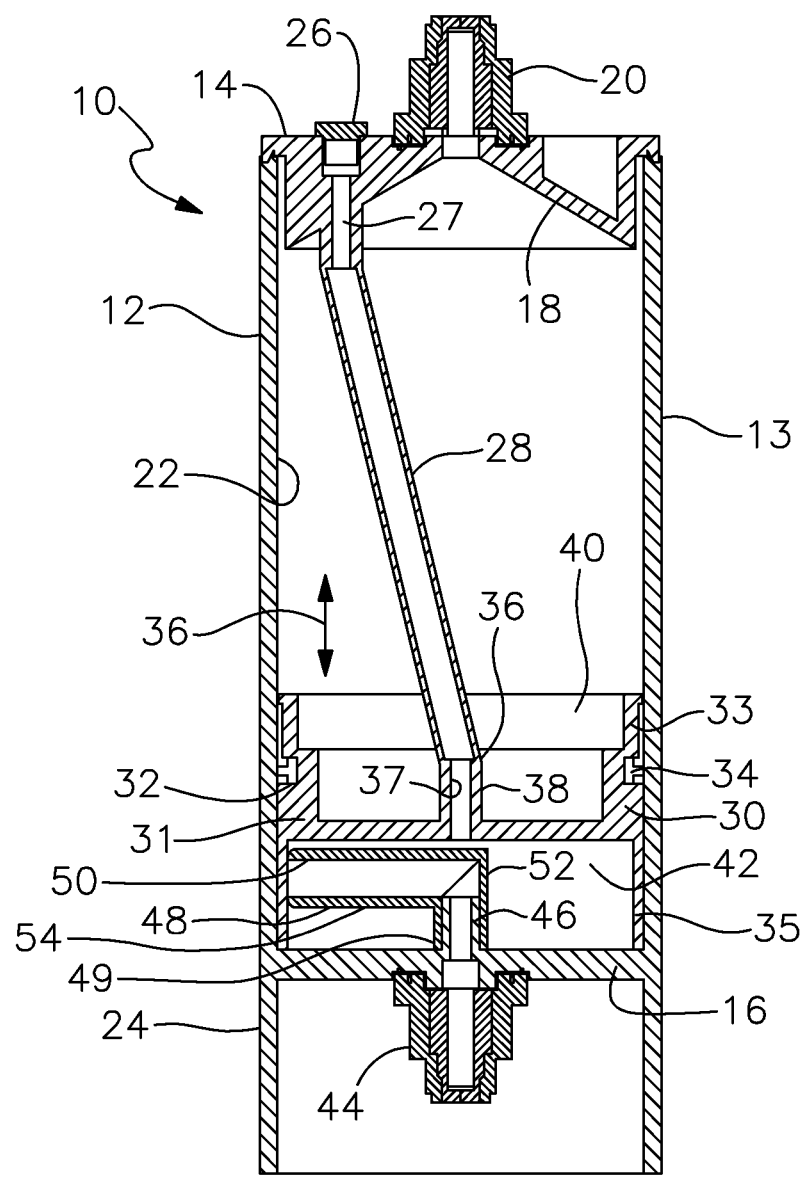
FIG. 1 is an elevational and cross-sectional front view of a preferred vented dual port centrifuge tube in accordance with this invention.
Figure 2:
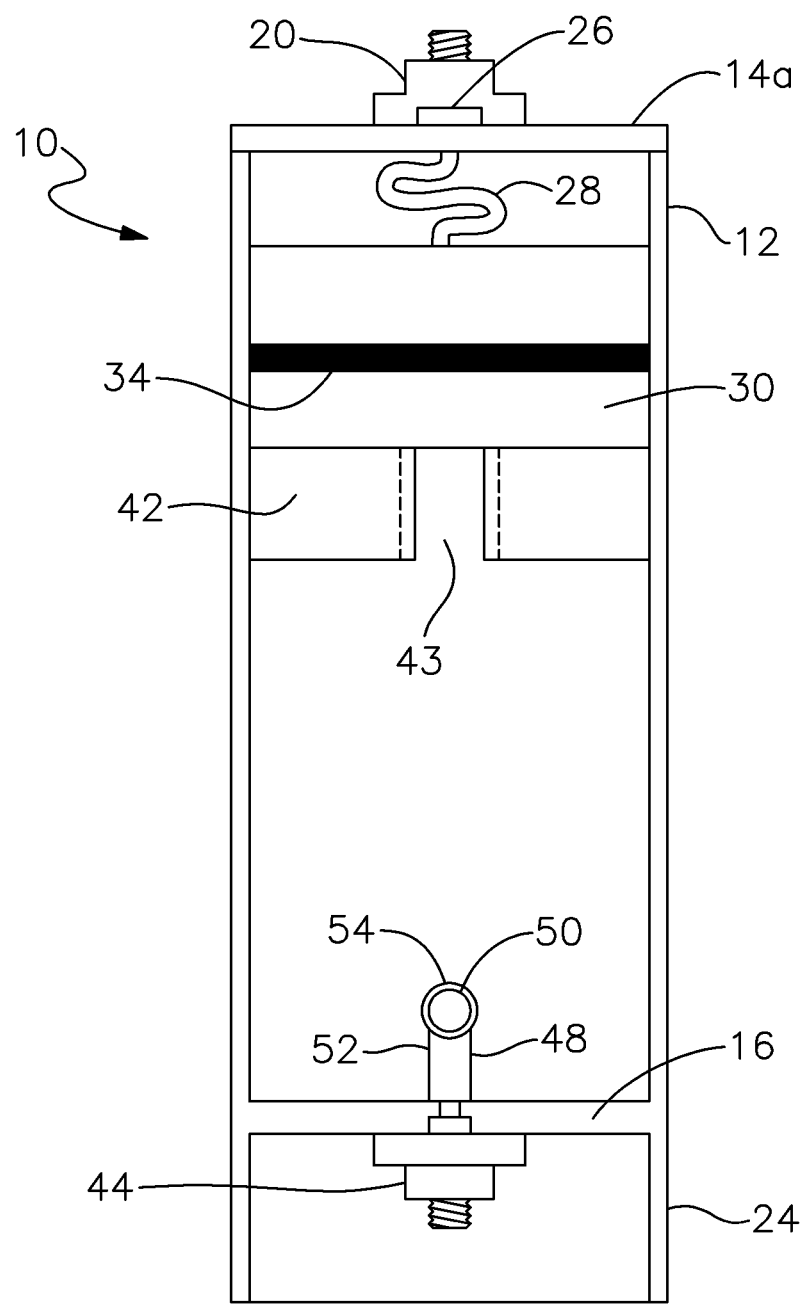
FIG. 2 is a simplified elevational side view of the tube of FIG. 1.
Figure 7:
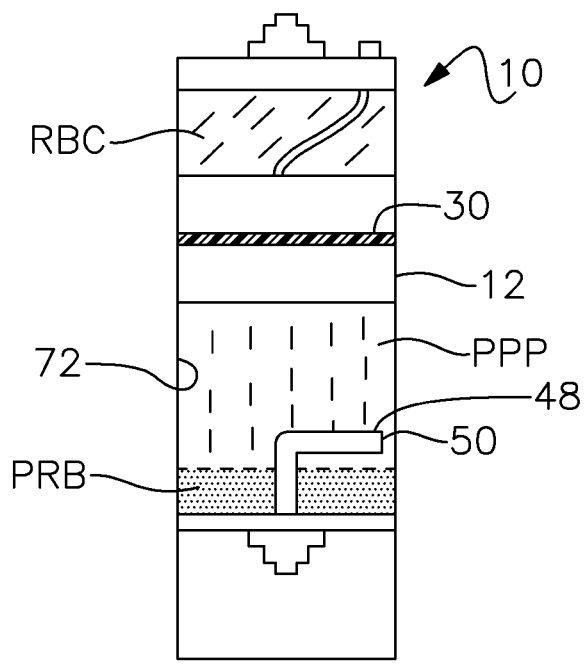
FIG. 7 is a similar elevational rear view of the preferred tube after it undergoes a second centrifugation to separate the constituent component in the lower chamber region into third and fourth constituent components, e.g., platelet poor plasma (PPP) and platelet rich buffy coat (PRB)

There is shown in FIGS. 1-2 a vented dual port centrifuge tube 10 that includes a tubular or cylindrical receptacle 12. The receptacle is defined by an elongate cylindrical sidewall 13 that extends between closed upper and lower end portions. The closed upper end portion comprises a cap 14 (FIG. 1) that may be either permanently or removably attached to sidewall 13. The lower end portion includes a generally planar floor 16 that is unitarily connected to sidewall 13 and extends across the bottom of the receptacle. As best depicted in FIG. 1, cap 14 preferably includes an interior opening 18 that has a generally truncated conical shape and communicates with a first common inlet and outlet port 20 to facilitate introduction and aspiration of biological fluids into and out of receptacle 12, as described more fully below. It should be noted that in certain embodiments, the configuration of the cap and cap opening may be simplified or otherwise modified. Indeed, in FIGS. 2-10, a simpler and generally planar cap 14a is disclosed. In such cases the port 20 may be communicably connected to the interior of receptacle 12 through a straight or otherwise alternatively shaped opening. It should be understood that in all versions of this invention, the cap or other upper end of tubular receptacle has an opening or passageway that defines or communicates with a syringe-engaging common inlet and outlet port for introducing and aspirating biological fluids into and out of the tubular receptacle 12 in accordance with this invention. Nonetheless, the particular configuration and construction of the upper end cap may be varied within the scope of this invention.

Receptacle 12 includes an interior chamber 22 that extends from floor 16 to cap 14. This chamber accommodates blood, chemicals, stem cells, bone marrow aspirate or other biological fluids/products to be centrifuged and aspirated using tube 10 the tube is particularly effective for sequestering and recovering high quality platelet rich plasma (PRP). Nonetheless, it may be employed effectively for separating and recovering various other fluid biological constituents within the scope of this invention.

As used herein "centrifuge" and "tube" should be understood to comprise assorted shapes and sizes of vessels, receptacles and containers having an interior chamber for holding a biological product and capable of being centrifuged to aspirate the product into constituent components. The vented dual port, single piston centrifuge tube disclosed herein is not limited to just tubular and elongate configurations, although such configurations will typically be used in preferred embodiments of this invention.

A cylindrical skirt 24 is connected unitarily with and depends from floor 16 and/or sidewall 13 of tubular receptacle 12. In alternative embodiments, skirt 24 may be separate from and releasably attached or affixed to the lower end of receptacle 12. The cylindrical skirt acts as a base, which stably supports the tubular receptacle in an upright condition on a table or other flat or horizontal surface. In this way, the centrifuge tube does not require a separate rack or holder for support. Cylindrical skirt 24 also securely supports the device upright in a standard centrifuge machine when the tube is centrifuged in accordance with the orientation depicted in FIGS. 4 and 7 as described more fully below.

Tubular receptacle 12 is typically composed of a durable plastic material such as polypropylene or other material suitable for medical or veterinary applications. The tube should be constructed to withstand the forces exerted by centrifuging. In certain applications, shatter-resistant glass may be employed.

A plurality of graduated volume markings, not shown herein, but see U.S. Pat. No. 7,976,796 (hereinafter '796), may be formed at various selected intervals along the exterior sidewall 13 of tubular receptacle 12. Such markings should be made at heights or intervals corresponding to commonly selected volumes of biological product that will be introduced into the tube. Such markings may be varied within the scope of this invention.

A vent 26 is formed through cap 14, 14a to communicably interconnect chamber 22 with the ambient air surrounding tube 10. Vent 26 may be constructed analogously to the vents disclosed in U.S. Pat. No. '796 and U.S. Pat. No. 10,300,481 (hereinafter '481). In particular, vent 26 may comprise a vent plug that fits through a hole in the cap. The vent is communicably connected with an elongate, flexible vent pipe 28 in order to equalize and neutralize pressure in receptacle 12 during the operation of tube 10 as described below. Vent 26 may feature a through channel that accommodates a filter for trapping contaminants that are pulled into receptacle 12 with the ambient air during operation of the tube, again as described below. Once again, this filter construction may be of the type disclosed in the above-referenced patents. Vent pipe 28 is composed of a flexible yet strong plastic material such as silicone that permits the pipe to be reliably flexed or collapsed during operation of tube 10.

In preferred versions of this invention, cap 14, 14a is permanently secured to the tubular receptacle. This may be accomplished by ultrasonic welding or other known methods. The upper end of the receptacle may also be formed by a cap or lid that is molded or otherwise formed unitarily with the cylindrical receptacle using techniques known to persons skilled in the art. Alternatively, the end cap may be releasably engaged with an open upper end of receptacle 12 in the manner for example shown in U.S. Pat. Nos. '481 and 10,987,672 (hereinafter '672). The cap may have a partially recessed upper surface as shown in FIG. 1, or a flat upper surface as depicted in the remaining figures. The truncated conical inlet 18 shown in FIGS. 1 and 2 operates analogously to the corresponding opening or channel depicted in U.S. Pat. No. '481 to facilitate introduction and aspiration of biological fluids into and out of the receptacle so that constituent components can be separated using the tube.

Vent 26 supports a tubular stem 27, FIG. 1, that is itself communicably interengaged with an upper end of flexible vent pipe 28. The opposite lower end 36 of pipe 28 is communicably connected to a tubular fitting 38 that extends generally centrally through a liquid impermeable piston 30, which piston is itself mounted for slidable reciprocating movement within chamber 22 of receptacle 12. As described more fully below, this provides for a wholly unique and particularly effective manner for equalizing or neutralizing pressure within tube 10 during the centrifugation and fluid separation process.

As previously indicated, first common inlet/outlet port 20 is formed in an upper portion of receptacle 12, preferably through cap 14, 14a. It should be understood that in alternative embodiments the first common inlet and outlet port may be formed elsewhere in the upper portion of the receptacle above piston 30. More particularly, first upper inlet/outlet port may comprise a conventional self-sealing construction and employ a standard luer port for releasably and securely interconnecting a hypodermic syringe to the port. Various forms of construction that may be used for the upper end cap 14 and the first common inlet/outlet port 20 are disclosed, for example, in U.S. Pat. No. 6,835,353 (hereinafter Pat. No. '353), Pat. Nos. '481, 796 and '672, the disclosures of which are incorporated herein by reference. Preferably, caps 14, 14a are composed of polypropylene or other material similar to that formed in the tubular receptacle itself. The common inlet/outlet port may be communicably attached to the caps or alternatively molded together with the cap in a single manufacturing process.

As shown in FIGS. 1 and 2, piston 30 has a generally cylindrical peripheral shape conforming to the interior shape of sidewall 13. The piston includes a body 31, FIG. 1, having upper and lower peripheral flanges 33 and 35 extending respectively upwardly and downwardly therefrom. Body 31 includes an annular peripheral groove 32, best shown in FIG. 2, that accommodates an O-ring or alternative seal 34, which sealingly and slidably interengages the interior surface of sidewall 13 of tubular receptacle 12. This allows piston 30 to move longitudinally through chamber 22 during operation of tube 10, as indicated by double headed arrow 36 in FIG. 1. Vent pipe 28 extends through an open upper compartment of piston 30 surrounded by flange 33 and the lower distal end 36 of pipe 28 communicably engages tubular fitting 38. This fitting is formed centrally and communicably through piston body 31 and features an air passageway 37 that interconnects pipe 28 to an open lower piston compartment 42 surrounded by flange 35. In this manner, the vent pipe 28 and interconnected vent 26 are communicably interconnected through open lower piston compartment 42 to a lower region of receptacle chamber 22 disposed beneath piston 30. This provides a unique and very effective means to vent and neutralize pressure in the lower region of chamber 22 during operation of tube 10 as described more fully below. As best shown in FIG. 2, a channel 43 is formed diametrically across lower compartment 42 of piston 30.

A lower, second common inlet and outlet port 44 is operatively and communicably connected to a lower region of chamber 22 beneath piston 30. In particular, inlet/outlet port 44 includes a tubular conduit or stem section 46 that is formed through floor 16 of receptacle 12 and extends longitudinally into interior chamber 22. Second inlet/outlet port 44 again includes a self-sealing valve port and luer-type interconnection analogous to previously described first port 20. Port 44 is attached to the exterior surface of receptacle floor 16 within skirt 24 and is communicatively connected through floor 16 to conduit 46, which extends upwardly from the floor of the receptacle. In alternative embodiments, conduit 46 may be formed separately from and connected to floor 16. In still other embodiments, conduit 46 may comprise an integral and unitary part of port 44. Conduit 46 itself is communicably joined to a tubular elbow 48. As best shown in FIG. 1, the proximal end of elbow 48 interengages floor 16. The distal end of elbow 48 is positioned proximate the interior sidewall surface of the receptacle chamber 22. Elbow includes a generally vertical portion 52 and a horizontal portion 54. As best shown in in FIG. 2, channel 43 formed diametrically through lower compartment 42 of piston 30 is generally aligned with the horizontal portion 54 of tubular elbow 48. Accordingly, when piston 30 is in an elevated condition as shown in FIG. 2, the piston 30 and diametric channel 43 are raised above and clear of elbow 48. When the piston is lowered within chamber 22, as shown in FIG. 1, tubular elbow 48 fits neatly within channel 43 of piston 30. This occurs during use and operation of tube 10 as described more fully below. Otherwise, the exterior connective portion of second common inlet and outlet port 44 supported below floor 16 is constructed and operates analogously to standard luer-type ports as referred to above and in the patents and applications referenced herein.

Prior to usage of tube 10, sealing piston 30 is typically elevated at least somewhat within chamber 22 of receptacle 12, although in some cases, it may be in the lowered condition shown in FIG. 1. Tube 10 is utilized to centrifuge a fluid biological product into its constituent components and then to aspirate one ore more of those components as shown in FIGS. 3-10. A preferred representative use for tube 10 is in the separation of a blood sample into constituent blood components. Typically, it is desirable to separate plasma and ultimately platelets, from red blood cells of a blood product in order to derive a highly concentrated platelet rich plasma (PRP) for use in various surgical, medical or veterinary applications. This process is performed using assembly 10 in the following manner.

Initially, the empty receptacle 12 is stood upright on its cylindrical base or skirt 24 upon an underlying table or platform. If a separate cover or closure is engaged with tube 10 or either of its ports 20, 44, the cover/closure is removed. Blood product B, FIG. 3, is then introduced into the interior chamber 22 of receptacle 12. Specifically, for example, a 60 ml or other sized hypodermic syringe containing the blood or other biological product is operably engaged with the first or upper self-sealing port 20 in a standard manner. See U.S. Pat. Nos. '353, '796 and '481. The luer port 20 holds the dispensing tip of the syringe in place so that the hypodermic syringe is securely engaged with tube 10. The syringe is then operated in a conventional manner to introduce blood product B to be separated through port 20 and into interior chamber 22 of receptacle 12, FIG. 3. As blood is introduced into upper region 60 of chamber 22, the increasing volume of blood pushes piston 30 downwardly through receptacle 12, as indicated by arrows 62. Blood product is added to the receptacle by the syringe in this manner until a selected level of fluid is injected/introduced into the receptacle. Typically, piston 30 is pushed until it engages or is proximate to floor 16 of receptacle 12. As previously described, tubular elbow 48 is enclosed by the descending piston 30 and specifically received in channel 43 (See FIGS. 1 and 2). Critically, as piston 30 is driven downwardly through the receptacle, flexible vent pipe 28 expands from the coiled or collapsed condition shown in FIG. 2 to the open and extended condition show in FIG. 3. As a result, the increased air pressure generated by piston 30 within the region of chamber 22 below piston 30 is effectively vented from the tube through pipe 28 and vent 26. Air pressure within tube 10 is effectively neutralized or equalized so that a smooth and stick/resistance-free operation is achieved. Finally, when a selected or desired volume of blood has been added to the receptacle, injection is stopped and the injecting syringe is disengaged from port 20. For human bloodwork, the selected volume of blood may be, for example, 50-60 mls. This volume is preferred because it typically yields approximately 7 mls of platelet rich plasma after the process is completed.

Tubular receptacle 12 is next placed in a centrifuge and counterbalanced by another tube placed in the centrifuge machine. Skirt 24 allows tube 10 to sit stably within the centrifuge. This helps the tube to remain properly balanced while it is being centrifuged. The tube is centrifuged for approximately 90 seconds (although this time as well as the speed of the centrifuge may be varied within the scope of this invention in a manner known to persons skilled in the art) and, as shown in FIG. 4, blood B is thereby separated within upper chamber region 60 into a top layer comprising largely platelet/plasma suspension (PPS) and a bottom layer (RBC) comprising primarily red blood cells. At this stage, typically at least 90% of the red blood cells in the blood product are separated from layer PPS and settle within layer RBC. Various known types of centrifuge machines may be employed for the initial centrifuging. A single round or multiple rounds of centrifuging may be utilized at this stage. After the first centrifuging stage is completed, tube 10 is removed from the centrifuge and again supported on its flat base or skirt 24. Both layers PPS and RBC are held securely in the upper space 60 of chamber 22 above piston 30.

A new syringe is next engaged with port 20 and operated as represented by arrow 66 in FIG. 5 to aspirate the PPS from upper space 60 of chamber 22. As indicated by arrow 70, this draws ambient air inwardly through vent 24 and vent pipe 28 into lower region 72 of chamber 22 beneath rising piston 30. This effectively counteracts and neutralizes the vacuum being drawn in lower chamber region 22 as the piston is pulled upwardly in response to the aspiration of PPS. Once again, pressure is equalized within the tube and there is much less potential for sticking of the piston and resistance to aspiration of the PPS. The aspiration operation is therefore smoother and facilitated. Aspiration continues in this manner until piston 30 generally reaches the boundary between the PPS and RBC layers. Aspiration is then discontinued and the aspiration syringe is disengaged from port 20. The red blood cells RBC remain segregated and constrained in diminished space 60 between piston 30 and cap 14.

The syringe holding the retrieved PPS is next engaged with second common inlet/outlet port 44 within skirt 24 according to FIG. 6. The syringe is operated to inject the sequestered PPS as indicated by arrow 74 through lower port 44 and connected elbow 48 into lower region 72 of chamber 22. This substantially fills lower chamber region 72 with the retrieved PPS component.

When all of the PPS is reinjected into the lower chamber region 72 of receptacle 12, the PPS syringe is disengaged from second inlet/outlet port 44 and receptacle 12 is again placed in a centrifuge machine. The tube is then further centrifuged for approximately 5 minutes, although this time may again be varied within the scope of the invention. For both centrifuging steps, centrifuge speeds and times may be adjusted in a manner that will be understood to those skilled in the art. As reflected in FIG. 7, the PPS injected into chamber region 72 is separated by the second centrifuging operation into an upper layer of platelet poor plasma (PPP) and a lower layer of platelet rich buffy coat (PRB). Tubular elbow 48 is constructed and positioned such that its distal end or tip 50 is held above the FRB layer and within the PPP layer.

Figure 8:
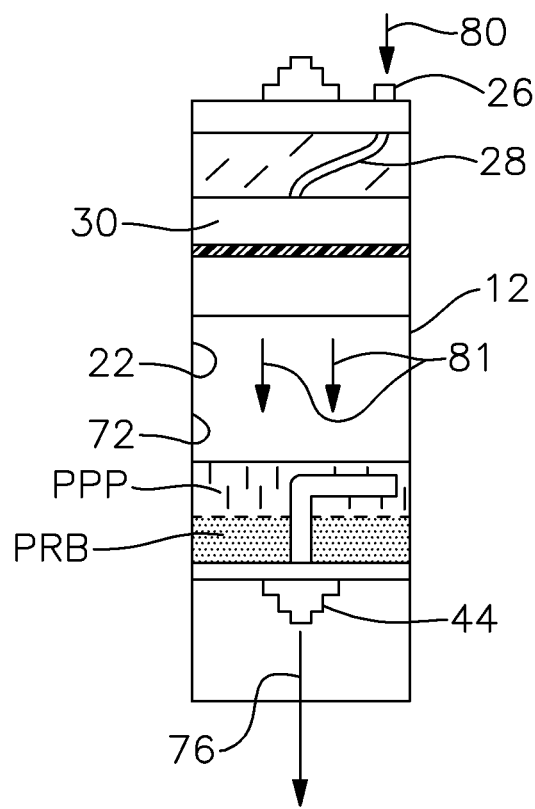
FIG. 8 is an elevational view of the tube similar to that shown in FIGS. 3-7 and which depicts the third constituent component being aspirated from the receptacle through the second common inlet and outlet port.

As represented in FIG. 8, a new syringe is interengaged with second common inlet/outlet port 44 and operated, as indicated by arrow 76, to aspirate PPP fluid from lower region 72 of chamber 22. Typically, the syringe is aspirated from receptacle 12 until a total of approximately 7 ml of fluid, consisting of 6 ml PPP and 1 ml PRB remains in chamber 22 below piston 30. These are typically the amounts remaining when an initial blood product volume of 50-60 mls is subjected to the two-stage centrifugation process in tube 10 as described above. Respective volumes may vary somewhat within the scope of this invention. As PPP is aspirated from tubular receptacle 12, ambient air is again drawn into the chamber through vent 26 and vent pipe 28 in the manner indicated by arrows 80. This again neutralizes pressure within lower region 72 of chamber 22 which facilitates aspiration of the PPP.

Figure 9:
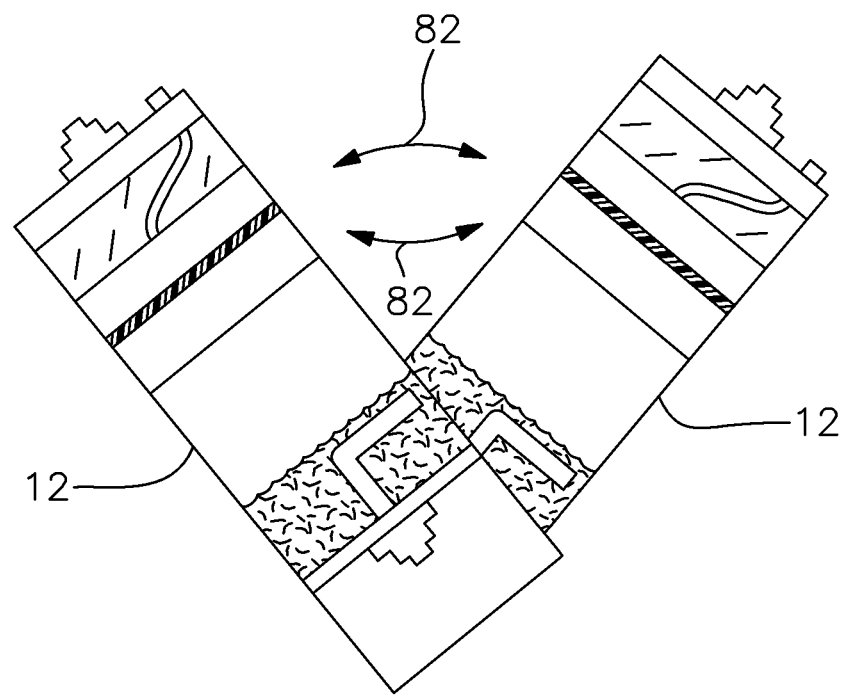
FIG. 9 is a similar elevational view that depicts agitation of the tube to mix the third and fourth constituent components remaining in the receptacle to form a final fluid constituent product to be recovered, e.g., platelet rich plasma (PRP)

The syringe containing the aspirated PPP is next disengaged from port 44. The platelets in the (e.g., 1 ml) platelet rich buffy coat layer PRB are then resuspended in the remaining (e.g., 6 ml) PPP layer contained in receptacle 12. This is typically accomplished as shown in FIG. 9 by swirling or otherwise gently agitating the tubular receptacle 12, as shown by double-headed arrows 82, so that the platelets of fluid layer PRB are effectively re-suspended into layer PPP. This produces a resulting volume of approximately 7 ml of pure and concentrated platelet rich plasma (PRP).

Figure 10:
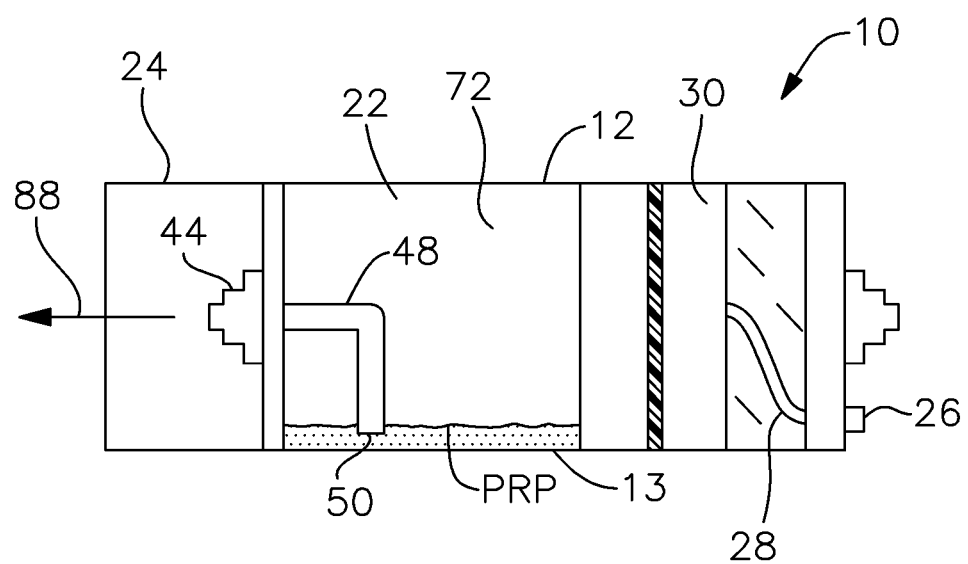
FIG. 10 is a view of the tube similar to that shown in FIGS. 3-9, which depicts the tube horizontally orientated for aspiration of PRP remaining in the receptacle.

Following re-suspension of the buffy coat in the platelet poor plasma to produce the desired PRP, receptacle 12 is oriented horizontally in the manner shown in FIG. 10. This positions supportive skirt 24 and second inlet/outlet port 44 such that tubular elbow 48 is oriented with its distal end or tip 50 positioned within the PRP collected against the now lower interior surface of sidewall 13 of receptacle 12. The user operatively connects a new syringe to the lower port 44 and aspirates the PRP, as indicated by arrow 88, through port 44 via tubular elbow 48. By positioning tip 50 of tubular elbow 48 very close to the interior surface of the sidewall 13, virtually all of the PRP (approximately 7 mls) contained in the receptacle can be aspirated from receptacle 12. This PRP has an extremely high platelet concentration and purity (approximately 80% or more). The aspirated PRP may then be utilized effectively for desired surgical, medical and veterinary applications. During the final aspiration step, the operation of the syringe is again facilitated because as PRP is withdrawn through elbow 48 and port 44, ambient air is introduced into region 72 of chamber 22 through vent 26, interconnected vent pipe 28 and tubular fitting 38 (FIG. 1) formed through piston 30. The pressure within the tube remains effectively equalized and neutralized. Resistance to movement of piston 30 is reduced and aspiration is facilitated.

An alternative vented dual port, single piston centrifuge tube 110 according to this invention is shown in FIGS. 11-17. The capacity, materials composing the tube and many if not most of the components comprising the tube are identical or analogous to those employed in the previously described embodiment. The most significant differences are described below.

Tube 110 includes a receptacle 112 featuring an upper portion that includes a cap 114 sealed or otherwise attached to an upper end of a cylindrical sidewall 113. Cap 114 supports a first, upper inlet and outlet port 120 and a vent 126. A vent pipe 128 is communicably connected to vent 126 in the manner previously described. Indeed, cap 114, port 120, vent 126 and vent pipe 128 are constructed in the manner previously described.

Receptacle 112 includes an interior chamber 122 that extends from cap 114 to a floor 116 at the lower end of receptacle 112. Unlike the previously described embodiment, sidewall 113 of receptacle 112 includes an interior lip or ledge 115 above floor 116 and surrounding a smaller diameter lower portion 117 of chamber 122.

A second common inlet and outlet port 144 is mounted to floor 116. Port 144 again includes exterior components 145 that feature a self-sealing luer port connection, which will be understood to persons skilled in the art. Port 144 further includes an interior channel 148 that is communicably interconnected to luer port connection 145. Tubular channel 148 is positioned within lower region 117 of receptacle chamber 122. The distal tip 150 of channel 148 is angled as shown in FIGS. 12-15. This allows the tube 110 to function in the fluid sequestration process as described below.

A semi-cylindrical skirt 124, which forms a base of tube 110, is interconnected to and depends from the lower end of receptacle 112. In contrast to the previously described embodiment, lower common inlet and outlet port 144 is offset from the center of the receptacle floor and is interconnected to floor 116 proximate sidewall 113 and at least partially outside of an arcuate slot formed in skirt 124. Skirt 124 again forms a base that supports receptacle 112 in an upright condition as shown in FIGS. 12-18. This provides the user with unhindered access to port 144 so that during use of tube 110, a syringe may be operably interconnected to port 145 for injecting fluids into and aspirating fluids from lower region 117 of chamber 122. This process is described more fully below.

Sequestration of biological fluids into constituent components and recovery of such components is performed using tube 110 in a manner analogous to that previously described for tube 10 in FIGS. 3-10. Once again, the process will be described for the recovery of high quality PRP from a blood sample. However, it should be understood that tube 110 may likewise be used to separate other biological fluids into discrete constituent components in an analogous fashion.

A liquid impermeable piston 130 is again slidably mounted within chamber 122 of receptacle 112. The piston may have a construction identical or similar to that of previously described piston 30. In the version shown herein, the piston includes a circumferential seal or O-ring 134 that interengages the interior surface of sidewall 13 such that piston 130 is able to slide longitudinally through chamber 122 while maintaining a seal between the upper and lower regions of the receptacle chamber. An air passageway fitting 138 is formed centrally through the piston between upper and lower ends thereof. Air passageway fitting 138 is communicably connected to a lower end of vent pipe 128. The air passageway fitting may be joined unitarily to the vent pipe as depicted in FIGS. 11-17. Alternatively, the vent pipe and air passageway fitting may comprise two separate pieces (see FIG. 1) that are communicably joined by fitting one inside the other, for example. Other alternative means for communicably coupling the vent pipe and air passageway fitting (e.g., tubular couplers) are also encompassed by this invention. The lower end of fitting 138 communicates with a conical or tapered opening 139 of piston 30. As a result, vent 126 is communicably linked to the lower region 117 of chamber 122, the region between the piston and floor 116 of receptacle 112.

Figure 11:
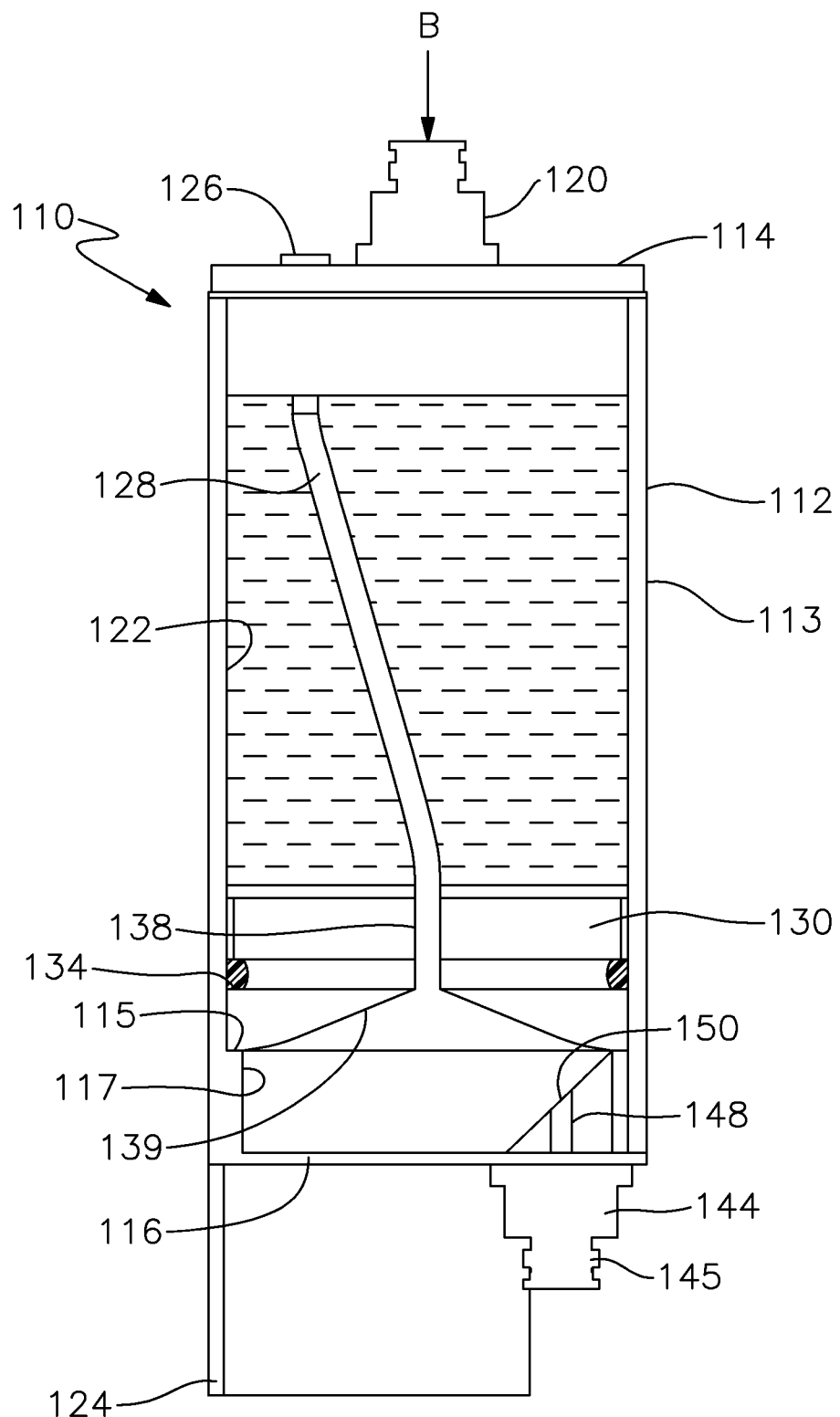
FIG. 11 is an elevational front view of an alternative centrifuge tube in accordance with this invention with a blood sample received in the chamber of the tubular receptacle above the piston.

As shown in FIG. 11, blood B is injected into the interior chamber of receptacle 112 through first port 120. The introduced blood drives piston 130 downwardly through receptacle 112. Typically, an upper region of chamber 122 fills with blood and piston 130 is pushed downwardly by the blood until the piston engages lip 115 of sidewall 113. This limits downward movement of the piston and restricts further introduction of blood into the chamber. As piston 130 moves downwardly, air in the lower region of the chamber is vented to the atmosphere through opening 139 and air passageway fitting 138 in piston 130, vent pipe 128 and vent 126. Pressure within the tube and particularly air pressure in the chamber region below piston 130 is equalized and the piston is operated by the user easily and without undue resistance or sticking within the receptacle. This facilitates the introduction of blood into tube 110 considerably.

Figure 12:
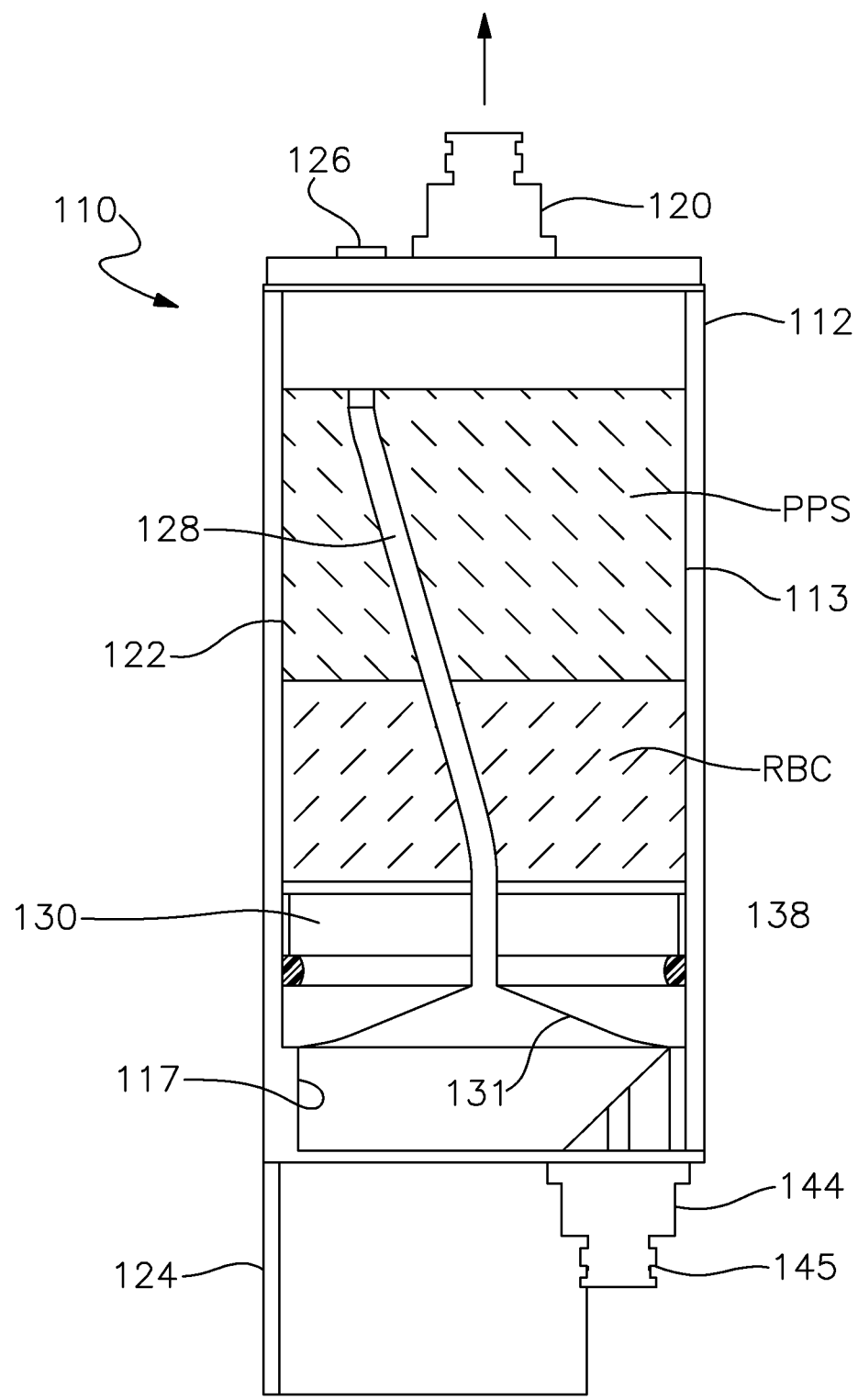
FIG. 12 is a similar view of the alternative tube after it has been centrifuged a first time to separate the blood sample into red blood cells and PPS.
Figure 13:
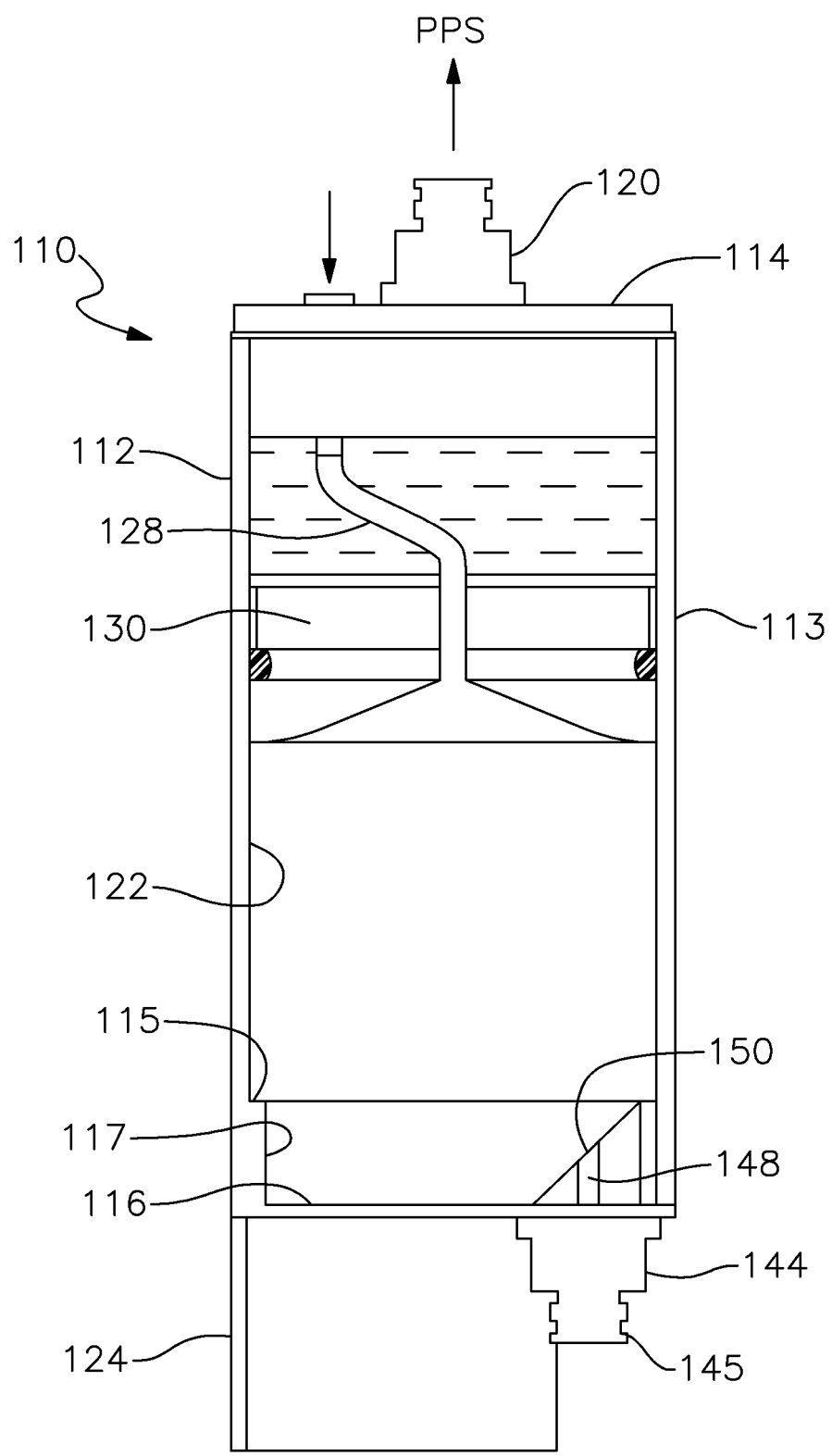
FIG. 13 is a view similar to FIGS. 11 and 12 that depicts the tube after the PPS has been aspirated from the receptacle and with the piston elevated and red blood cells being constrained within the upper chamber region of the receptacle above the piston.

After 50-60 mls or other volume of blood is introduced into the upper region of chamber 122 the syringe is removed from port 120 and tube 110 is placed in a centrifuge machine, which is operated fora predetermined time and at a selected speed to separate blood B into constituent components. Skirt 124 stably balances the tube as it is centrifuged. As shown in FIG. 12, the first centrifugation separates the blood into a lower level of red blood cells (RBC) and an upper level of plasma platelet suspension (PPS). As previously described and as further illustrated in FIG. 13, a new syringe is attached to port 120 and aspirated to remove the PPS from tube 110. Vent pipe 128 collapses and atmospheric air is permitted to enter the region of chamber 122 below piston 130. This neutralizes pressure in the lower region of the chamber and facilitates aspiration of the PPS.

Figure 14:
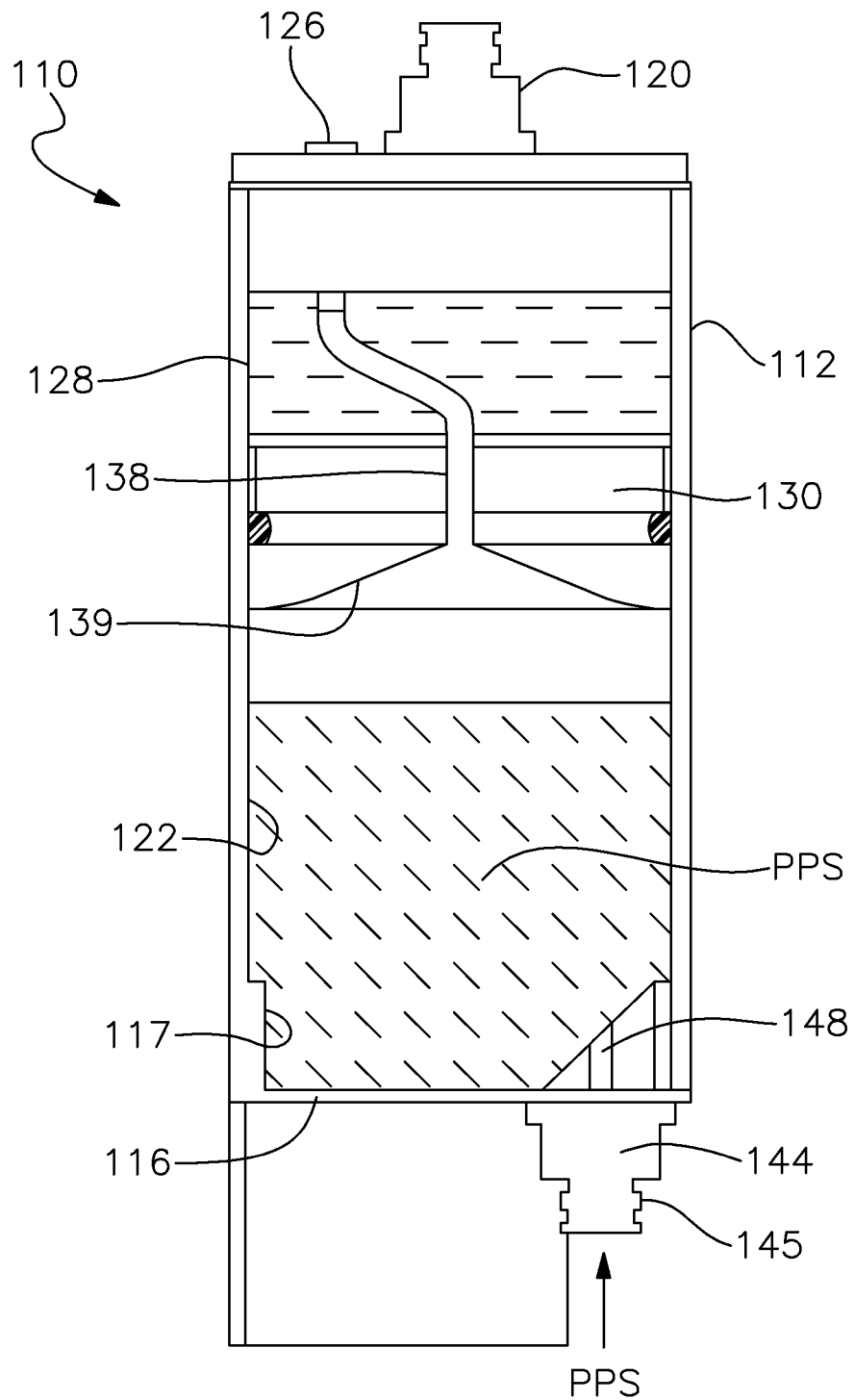
FIG. 14 is a view similar to FIGS. 11-13 and further depicting PPS being introduced into the lower region of the receptacle chamber beneath the piston.

As depicted in FIG. 14, the PPS previously removed through port 120 is reintroduced into tube 110 through the lower second port 144. In particular, the syringe containing the PPS is connected to exterior luer port connection 145 of port 144. The syringe is operated to inject the PPS through luer connection 145 and channel 148 into receptacle chamber 122 including narrower diameter lower region 117. Air within the region of the chamber between piston 130 and floor 116 is vented through the open bottom 139 and air passageway fitting 138, as well as communicably connected vent pipe 128 and vent 126. Pressure is thereby equalized within the chamber so that injection of the PPS is facilitated.

Figure 15:
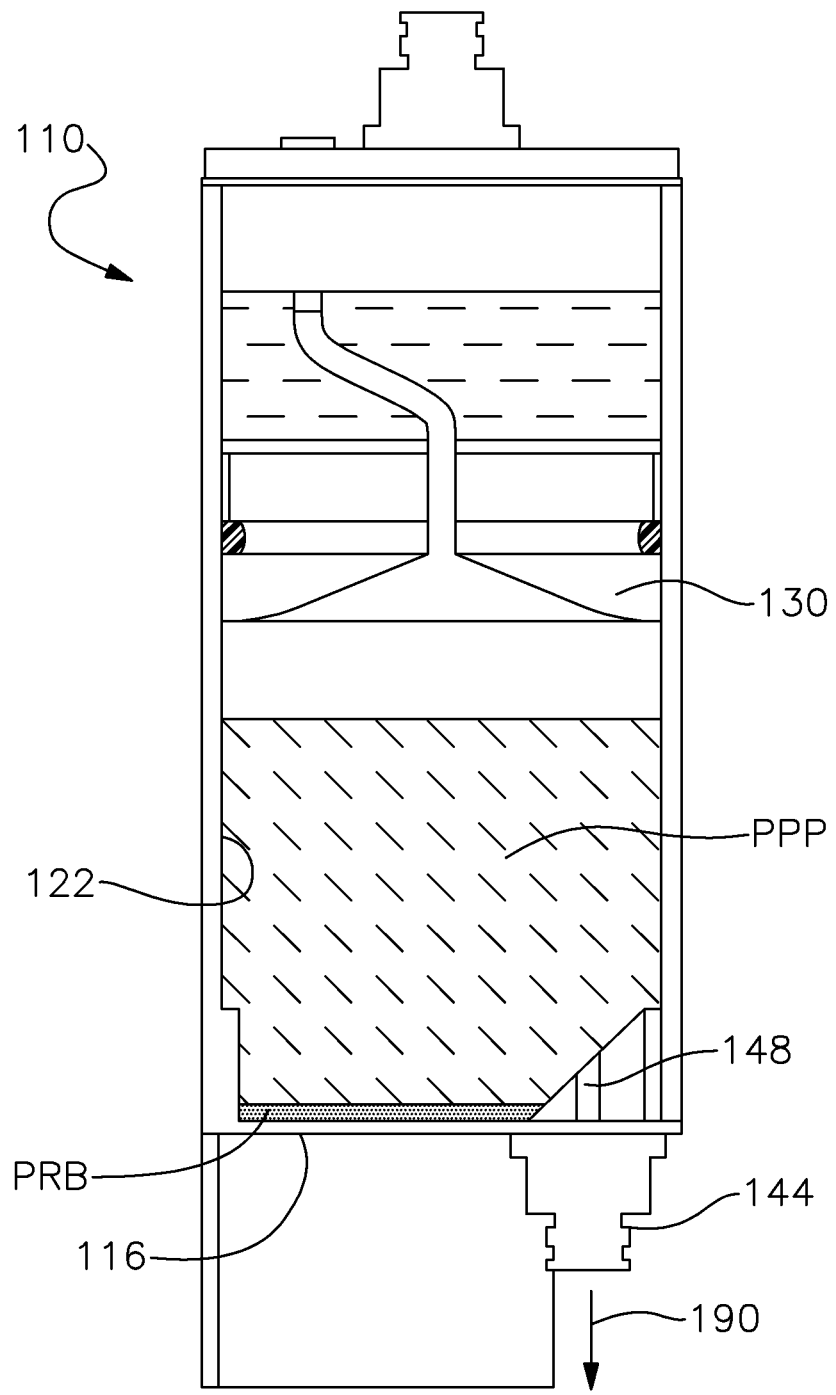
FIG. 15 is a view similar to FIGS. 11-14 after the tube has undergone a second centrifugation to separate the PPS into an upper layer of PPP and a lower layer of PRB.
Figure 16:
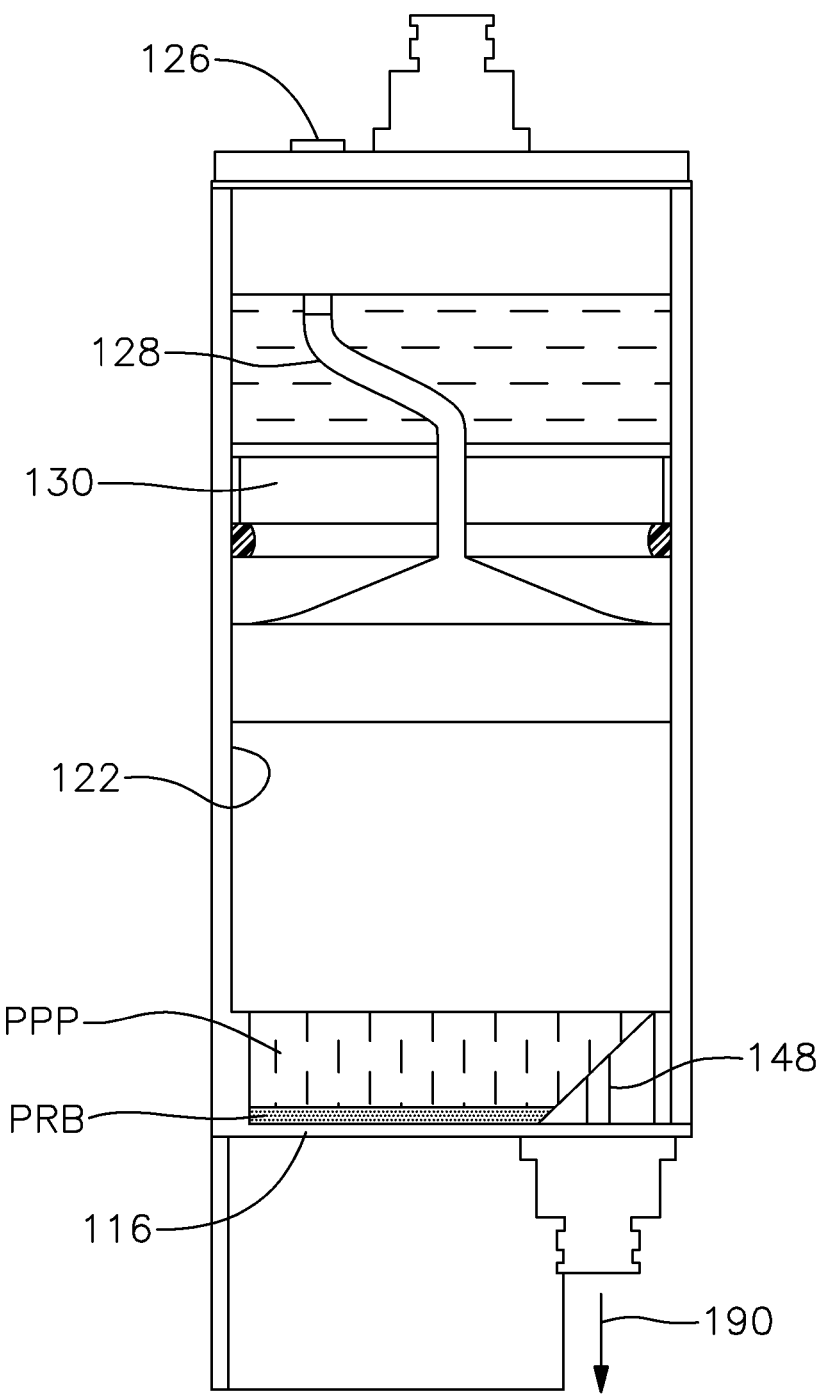
FIG. 16 is a similar view of the alternative tube with the PPP drawn down to a level such that the total fluid remaining in the lower region of the receptacle chamber is less than 7 ml.

The PPS syringe is then disconnected from port 144 and tube 110 is centrifuged again for a predetermined time and at a selected speed. This separates the PPS in the lower region of chamber 122 as shown in FIG. 15. Specifically, an upper layer of PPP is formed above a lower layer of PRB. At this point, the upper end of angled channel 148 is disposed within the PPP layer. The user attaches a new aspirating syringe to port 144 and aspirates PPP from tube 110, as indicated by arrow 190. Typically, the PPP is drawn down until approximately 7 ml of total fluid (PRB PPP) remains in the chamber between piston 130 and floor 116. See FIG. 16. Vent 126 and vent pipe 128 communicably interconnect the atmospheric/ambient air to the lower region of chamber 122 beneath piston 130. This neutralizes pressure in the chamber and again facilitates aspiration of the PPP from the tube.

Figure 17:
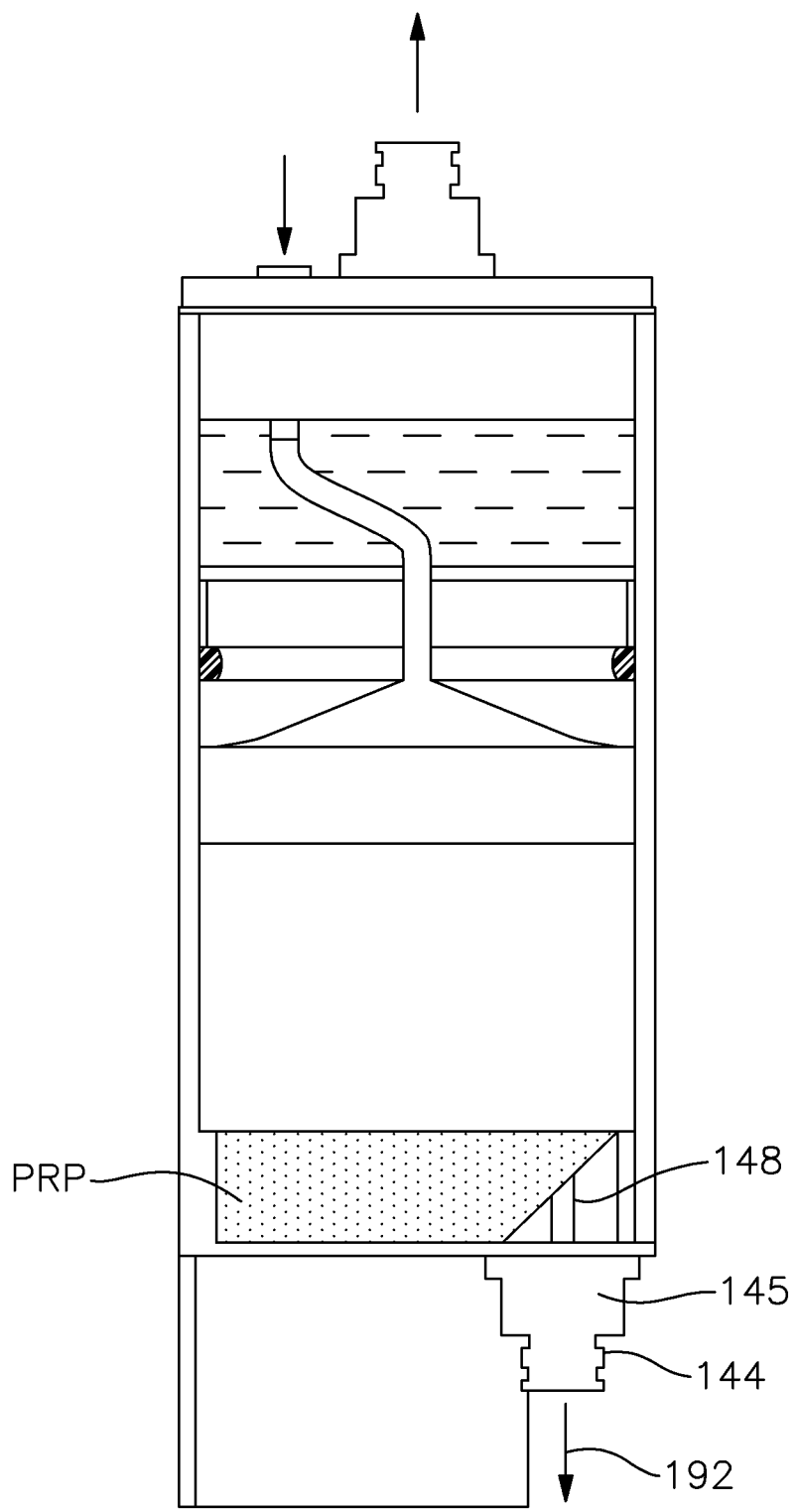
FIG. 17 is a similar view of the alternative tube after the remaining fluid components in the lower region of the receptacle chamber (e.g., PPP and PRB) have been mixed to produce a high quality PRP that is aspirated from the receptacle through the second common inlet and outlet port.

With approximately 7 ml of fluid remaining in the lower region of chamber 122, the tube is swirled or agitated as previously described, to mix the PPP and PRB remaining in the tube. This produces a high quality platelet rich plasma (PRP), as shown in FIG. 17. A new aspirating syringe is attached to lower second port 144. That syringe is operated to aspirate the PRP through channel 148 and self-sealing luer lock connection 145, as indicated by arrow 192. The recovered PRP may then be used for required medical and veterinary purposes. The unique vented construction employed by tube 110 again facilitates the final aspiration of PRP.

It should be further understood that the vented dual port, single piston centrifuge tube of this invention may employ additional and alternative assorted features and components as depicted in the above-referenced devices shown in U.S. Pat. Nos. '353, '796, '481 and Application No. '053. Moreover, various other modifications may be made within the scope of the invention. For example, the vent and/or one or both of the common inlet and outlet ports may be formed in the sidewall of the tubular receptacle. The terms "upper end", "upper portion", "lower end" and "lower portion" as used herein should be construed broadly to encompass portions of the sidewall of the tubular receptacle proximate the opposing longitudinal ends thereof.

Accordingly, the present invention provides for a vented, dual port, single piston centrifuge tube that is effective for producing a concentrated, pure and high quality PRP and which is operated easily and without undue or unwanted resistance or sticking. The unique venting system of the present invention, wherein a vent pipe is formed between a vent to the atmosphere and a lower region of the receptacle chamber situated below the piston, contributes significantly to this improved operation. In addition to producing high quality PRP, the tube may be employed analogously for separating other biological fluids into their constituent components and for aspirating these separated components from the fluids. The derived aspirates may be employed for a wide variety of surgical, medical and veterinary applications.

From the foregoing, it may be seen that this invention provides for a method and system for more effectively and efficiently concentrating blood platelets and other constituents and biological fluids for use in medical and other applications. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed is:

1. A vented dual port centrifuge tube for separating and aspirating constituent components of a fluid biological product, the vented dual port centrifuge tube comprising:
   a receptacle having upper and lower end portions and an interior chamber extending between said upper and lower end portions;
   a liquid impermeable piston mounted within said receptacle and sealably engaging an interior side wall of said receptacle, said chamber consisting of a single upper region and a single lower region, which upper and lower regions are separated by said piston, said upper region located above said piston and extending from a top of said piston to said upper end portion of said receptacle, said lower region located below said piston and extending from a bottom of said piston to said lower end portion of said receptacle, said piston being movable through said chamber between said upper and lower end portions;
   a first common inlet and outlet port formed in said upper end portion of said receptacle, said first common inlet and outlet port adapted to selectively introduce the fluid biological product exclusively into said upper region of said chamber and aspirate a first constituent component of the fluid biological product from said upper region of said chamber after said receptacle is centrifuged a first time to separate the first constituent component from the fluid biological product;
   a second common inlet and outlet port formed in said lower end portion of said receptacle, said second common inlet and outlet port adapted to selectively introduce the aspirated first constituent component into said lower region of said chamber and aspirate a second constituent component from said lower region of said chamber after said receptacle is centrifuged a second time to separate the second constituent component from the first constituent component;
   a vent formed through said upper end portion of said receptacle; and
   a vent pipe attached to said vent and engaging said piston, said vent pipe communicably interconnecting said vent exclusively with said lower region of said chamber, whereby air pressure exclusively in said lower region of said chamber is equalized through said vent pipe and said communicably interconnected vent when the fluid biological product is introduced into said upper region of said chamber, when the first constituent component is respectively aspirated from said upper region and introduced into said lower region of said chamber, and when the second constituent component is aspirated from said lower chamber region.

2. The vented dual port centrifuge tube of claim 1 in which said upper end portion of said receptacle includes a cap defining said upper end portion and supporting said pressure equalizing vent and said first common inlet and outlet port, said vent being spaced apart and distinct from said first common inlet and outlet port.

3. The vented dual port centrifuge tube of claim 1 in which said lower end portion of said receptacle includes a substantially flat base through which said lower common inlet and outlet port is formed to communicate with said second region of said chamber.

4. The vented dual port centrifuge tube of claim 1 in which an air passageway is formed through said piston, which air passageway is communicably interconnected between said vent pipe and said lower region of said chamber.

5. The vented dual port centrifuge tube of claim 1 in which said piston includes a channel extending diametrically across a said bottom of said piston, said second common inlet and outlet port being communicably connected within said lower region of said chamber to a tubular elbow, which elbow includes a vertical portion and a horizontal portion communicably connected to said vertical portion, said channel of said piston being aligned with said horizontal portion of said elbow, said piston being lowered in said chamber proximate said lower end portion of said receptacle such that said horizontal portion of said tubular elbow is received by said channel when the fluid biological product is introduced into said upper region of said chamber and said piston is raised in said chamber when the first constituent element is aspirated from said upper region of said chamber such that said horizontal portion of said tubular elbow is exposed by said channel and an open distal tip of said elbow is disposed adjacent to and faces an inner sidewall surface of said receptacle.

6. The vented dual port centrifuge tube of claim 5 in which said piston includes a piston body and upper and lower circumferential flanges that are attached to and extend upwardly and downwardly respectively from said piston body, said channel extending across said lower circumferential flange.

7. The vented dual port centrifuge tube of claim 1 further including a base attached to and depending from said upper end portion of said receptacle, said base having a cylindrical shape and said second common inlet and outlet port being surrounded by and positioned centrally within said base.

8. The vented dual port centrifuge tube of claim 1 in which said second common inlet and outlet port is centrally offset within said lower end portion of said receptacle.

9. The vented dual port centrifuge tube of claim 8 in which said second inlet and outlet port includes a vertical tubular channel that extends into said lower region of said chamber, said tubular channel having a slanted tip to facilitate aspiration of constituent components from said lower region of said chamber.

10. The vented dual port centrifuge tube of claim 1 in which said piston includes a generally conically shaped opening that is communicably connected to said vent pipe and which faces said lower region of said chamber.

11. The vented dual port centrifuge tube of claim 1 in which said receptacle includes an elongate tubular configuration.

12. The vented dual port centrifuge tube of claim 1 in which said vent pipe is collapsible.

13. The vented dual port centrifuge tube of claim 1 in which said vent pipe is longitudinally flexible.

14. A vented dual port centrifuge tube for separating and aspirating constituent components of a fluid biological product, the vented dual port centrifuge tube comprising:

a receptacle having upper and lower end portions and an interior chamber extending fully between said upper and lower end portions;

a single liquid impermeable piston mounted within said receptacle and sealably engaging an interior side wall of said receptacle, said chamber consisting of a single upper region and a single lower region separated by said piston, said upper region located above said piston and extending from a top of said piston to said upper end portion of said receptacle, said lower region located below said piston and extending from a bottom of said piston to said lower end portion of said receptacle, said piston being movable through said chamber between said upper and lower end portions;

a first common inlet and outlet port formed in said upper end portion of said receptacle, said first common inlet and outlet port adapted to selectively introduce the fluid biological product exclusively into said upper region of said chamber and aspirate a first constituent component of the fluid biological product from said upper region of said chamber after said receptacle is centrifuged a first time to separate the first constituent component from the fluid biological product;

a second common inlet and outlet port formed in said lower end portion of said receptacle, said second common inlet and outlet port adapted to selectively introduce the aspirated first constituent component into said lower region of said chamber and aspirate a second constituent component from said lower region of said chamber after said receptacle is centrifuged a second time to separate the second constituent component from the first constituent component;

a single vent formed through said upper end portion of said receptacle; and a single vent pipe attached to said vent and engaging said piston, said vent pipe communicably interconnecting said vent exclusively with said lower region of said chamber such that said lower region is vented and said upper region is unvented, whereby air pressure exclusively in said lower region of said chamber is equalized through said vent pipe and said communicably interconnected vent when the fluid biological product is introduced into said upper region of said chamber, when the first constituent component is respectively aspirated from said upper region and introduced into said lower region of said chamber, and when the second constituent component is aspirated from said lower chamber region.

15. A method for separating a fluid biological product into constituent components using a centrifuge tube assembly, which assembly includes an elongate tubular receptacle having closed upper and lower ends, a liquid impermeable piston mounted within the tubular receptacle and sealingly engaging the interior surface of the tubular receptacle for longitudinally sliding through the chamber of the tubular receptacle between the upper and lower ends, the centrifuge tube assembly further including a first common inlet and outlet port formed in the upper end of the receptacle for communicating with the interior chamber of the receptacle, a second common inlet and outlet port formed through the lower end of the tubular receptacle and communicating with the chamber, and a vent formed in the upper end of the tubular receptacle and communicably interconnected by a flexible vent pipe that extends through said piston to a lower region of said tubular receptacle chamber between said piston and the lower end portion of the tubular receptacle, said method comprising:

Introducing the fluid biological product into said receptacle through said first common inlet and outlet port such that the piston is driven downwardly within said chamber and pressure in the lower chamber region is equalized through the vent pipe and the vent;

centrifuging the tubular receptacle first time to separate the fluid into at least two constituent components;

aspirating a first constituent component from the upper chamber region of the receptacle chamber through the first common inlet and outlet port such that suction is generated in the lower chamber region and ambient air is introduced through the vent and vent pipe into the lower chamber region to equalize the air pressure therein;

introducing the aspirated constituent component into the lower chamber region through the second common inlet and outlet port such that air in the lower chamber region is discharged through the vent tube and vent to equalize pressure within the tube;

centrifuging the tube a second time to separate the first constituent component into second and third constituent components; and aspirating at least one of the second and third constituent components through the second common inlet and outlet port.

* * * * *